(12) United States Patent
Engelke et al.

(10) Patent No.: US 9,618,472 B2
(45) Date of Patent: Apr. 11, 2017

(54) METHOD AND DEVICES FOR OPERATING A HEATABLE EXHAUST-GAS SENSOR

(71) Applicant: Robert Bosch GmbH, Stuttgart (DE)

(72) Inventors: Frank Engelke, Stuttgart (DE); Claudius Bevot, Stuttgart (DE); Thomas Schulz, Bietigheim-Bissingen (DE); Rolf Reischl, Stuttgart (DE); Ralf Kraemer, Kusterdingen (DE); Andreas Gess, Comaringen (DE)

(73) Assignee: ROBERT BOSCH GMBH, Stuttgart (DE)

( * ) Notice: Subject to any disclaimer, the term of this patent is extended or adjusted under 35 U.S.C. 154(b) by 129 days.

(21) Appl. No.: 14/388,141

(22) PCT Filed: Feb. 14, 2013

(86) PCT No.: PCT/EP2013/052972
§ 371 (c)(1),
(2) Date: Jan. 13, 2015

(87) PCT Pub. No.: WO2013/143767
PCT Pub. Date: Oct. 3, 2013

(65) Prior Publication Data
US 2015/0114848 A1 Apr. 30, 2015

(30) Foreign Application Priority Data
Mar. 27, 2012 (DE) .................. 10 2012 204 899

(51) Int. Cl.
G01N 27/403 (2006.01)
G01N 27/406 (2006.01)
G01M 15/10 (2006.01)

(52) U.S. Cl.
CPC ........ *G01N 27/403* (2013.01); *G01M 15/102* (2013.01); *G01N 27/4067* (2013.01)

(58) Field of Classification Search
CPC ............ G01N 27/4067; G01N 27/403; G01M 15/102
See application file for complete search history.

(56) References Cited

U.S. PATENT DOCUMENTS

| 5,759,367 A | 6/1998 | Matsuura et al. |
| 6,289,719 B1 * | 9/2001 | Bloemer ............ G01N 27/4067 204/424 |
| 2004/0045824 A1 | 3/2004 | Hada et al. |

FOREIGN PATENT DOCUMENTS

| CN | 1158996 A | 9/1997 |
| CN | 101240753 A | 8/2008 |

(Continued)

OTHER PUBLICATIONS

International Search Report for PCT/EP2013/052972, dated May 7, 2013.

*Primary Examiner* — Arun S Phasge
(74) *Attorney, Agent, or Firm* — Gerard Messina

(57) ABSTRACT

In a method for operating a heatable exhaust-gas sensor, which supplies at least one measuring signal and in which a sensor heater is operated using a pulse-width modulated operating voltage, the detection of the at least one measuring signal has priority over the supply of the pulse-width modulated operating voltage for sensor heater, and at least during a predefined time window in which the measuring signal is detected, the supply of the pulse-width modulated operating voltage for the sensor heater is suppressed using a blocking signal.

11 Claims, 3 Drawing Sheets

(56) References Cited

FOREIGN PATENT DOCUMENTS

| CN | 101685078 A | 3/2010 |
|---|---|---|
| DE | 197 43 644 | 4/1999 |
| DE | 10 2008 042268 | 4/2010 |
| JP | 11006813 | 1/1999 |
| JP | 2001508880 A | 7/2001 |
| JP | 2003050226 A | 2/2003 |
| JP | 2006113081 A | 4/2006 |
| JP | 2008203190 A | 9/2008 |

* cited by examiner

METHOD AND DEVICES FOR OPERATING A HEATABLE EXHAUST-GAS SENSOR

BACKGROUND OF THE INVENTION

1. Field of the Invention The present invention relates to a method and a device for operating a heatable exhaust-gas sensor.

2. Description of the Related Art

Exhaust-gas sensors such as lambda or NO sensors for example are used for operating internal combustion engines, the sensor signals of which are used to control the internal combustion engine in order to ensure, for example, suitable conditions for an effective emission control in an emission control system.

Particularly exhaust-gas sensors that have an ion-conducting solid electrolyte, such as lambda or $NO_x$ sensors for example, require a specific operating temperature in order to achieve the necessary ionic conductivity of the solid electrolyte.

Additionally, the measuring accuracy depends on the temperature of such a sensor. For this reason it is generally necessary to heat the probe and check the temperature and normally to regulate it. To measure the temperature, one normally does without a separate thermal element. Instead, it is possible for example to make use of the highly temperature-dependent internal resistance $R_i$ of the exhaust-gas probe in order to obtain a measuring signal for the sensor temperature. Another measuring signal, which is provided by the heatable exhaust-gas sensor, is for example the Nernst voltage, which allows for an inference as to whether a measuring gas found on the electrodes is thermodynamically balanced.

Due to the comparatively high operating currents of a sensor heater, which is normally operated using a pulse-width modulated voltage, disturbances caused by the pulse edges may occur, which may influence the at least one measuring signal provided by the heated exhaust-gas sensor.

Published German patent application document DE 10 2008 042 268 A1 describes a method for operating a heatable exhaust-gas sensor, in which the detection of the measuring signals is defined as a function of the pulse-width modulated operating voltage of the sensor heater. The detection of the at least one measuring signal is defined as a function of the edges of the pulse-width modulated operating voltage of the sensor heater in such a way that a certain waiting period is specified after the occurrence of a rising or falling pulse edge before the measuring signal is detected.

The present invention is based on the objective of indicating a method and devices for operating a heatable exhaust-gas sensor, in which the sensor heater is operated using a pulse-width modulated operating voltage and in which the at least one detected measuring signal is disturbed as little as possible by the pulse-width modulated operating voltage of the sensor heater.

BRIEF SUMMARY OF THE INVENTION

The procedure of the present invention for operating a heated exhaust-gas sensor is based on the fact that the heatable exhaust-gas sensor provides at least one measuring signal and that the sensor heater is operating using a pulse-width modulated operating voltage. The procedure according to the present invention is distinguished by the fact that the detection of the at least one measuring signal has priority with respect to the pulse-width modulated operating voltage of the sensor heater and that in a designated measuring signal detection within a measuring window the provision of the pulse-width modulated operating voltage for the sensor heater is suppressed by a blocking signal.

The measures provided according to the present invention on the one hand allow for a specifiable high rate in the detection of the at least one measuring signal provided by the heated exhaust-gas sensor and allow on the other hand for a high suppression of possible disturbances of the at least one measuring signal particularly emanating from the switching edges of the pulse-width modulated operating voltage of the sensor heater.

The devices according to the present invention for implementing the method either provide only for an exhaust-gas sensor electronic system or both for an exhaust-gas sensor electronic system and a separate control unit.

If only an exhaust-gas sensor electronic system is provided, then the exhaust-gas sensor electronic system contains both a measuring signal evaluation device and a pulse-width modulator, the measuring signal evaluation device providing the blocking signal and making it available to the pulse-width modulator.

If an exhaust-gas sensor electronic system and a separate control unit are provided, then the exhaust-gas sensor electronic system contains the measuring signal evaluation device and the control unit contains the pulse-width modulator. This development is used in particular if the exhaust-gas sensor electronic system is situated near the heatable exhaust-gas sensor, for example in a plug.

A first alternative of this device provides for the measuring signal evaluation device contained in the exhaust-gas sensor electronic system to supply the blocking signal and for the blocking signal to be conducted to the switching device, which contains the pulse-width modulator, to which the blocking signal is provided.

Another alternative of this device provides for the exhaust-gas sensor electronic system and the separate switching device to operate in clock-synchronized fashion, for the switching device to contain a sequence control system, which has information about the measuring signal detection within the measuring windows such that the exhaust-gas sensor electronic system does not have to supply a blocking signal to the switching device and instead the sequence control system supplies the blocking signal directly to the pulse-width modulator contained in the switching device.

Exemplary embodiments of the present invention are depicted in the drawing and explained in greater detail in the description below.

DETAILED DESCRIPTION OF THE INVENTION

Figure 1:
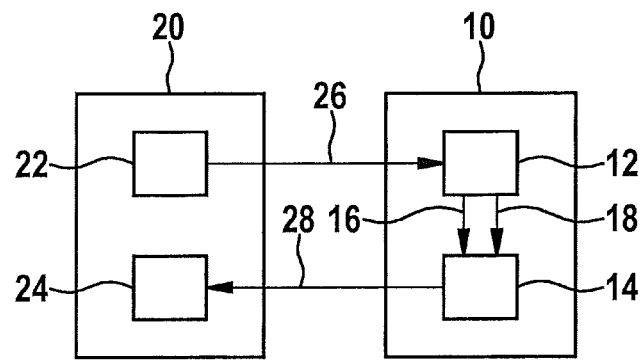
FIG. 1 shows a simple development of a device according to the present invention having a heatable exhaust-gas sensor and an exhaust-gas sensor electronic system.

FIG. 1 shows a simple development of a device according to the present invention having an exhaust-gas sensor electronic system 10, which contains a measuring signal evaluation device 12 as well as a pulse-width modulator 14. Measuring signal evaluation device 12 supplies pulse-width modulator 14 both with a temperature signal 16 as well as with a blocking signal 18.

A heatable exhaust-gas sensor 20 containing a measuring signal detection device 22 as well as a sensor heater 24 is also provided. Measuring value detection device 22 supplies at least one measuring signal 26 to measuring signal evaluation device 12. Pulse-width modulator 14 supplies a pulse-width modulated operating voltage 28 to sensor heater 24.

Figure 2A:
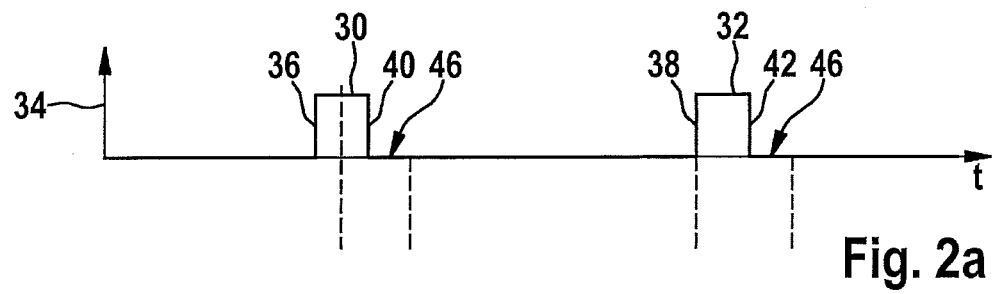
FIG. 2a shows a time lapse of measuring signal detection processes.
Figure 2B:
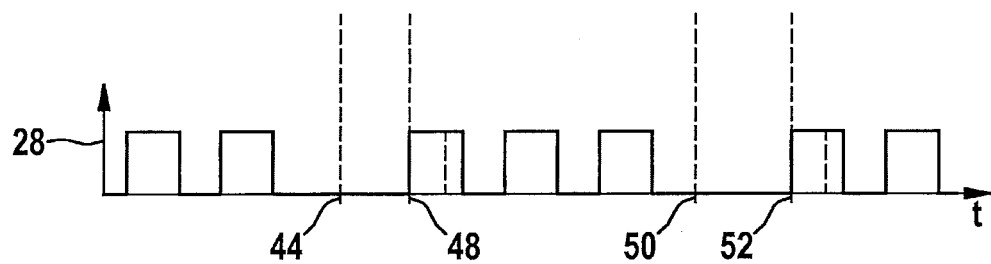
FIG. 2b shows a pulse-width modulated operating voltage.

The method of functioning of the device shown in FIG. 1 is explained in more detail with reference to the signal patterns shown in FIGS. 2a and 2b as a function of time t. In this instance, FIG. 2a shows a time lapse of measuring signal detection processes and FIG. 2b shows the pulse-width modulated operating voltage 28.

Heatable exhaust-gas sensor 20 is, for example, a lambda sensor, an HC sensor, an NH3 sensor or an NOx sensor. Sensor heater 24 ensures that measuring value detection device 22 is heated to the required operating temperature, which in most cases is above the exhaust-gas temperature. The operating temperature of measuring value detection device 22 may be up to 850 degree Celsius for example. For setting the operating temperature, the pulse-width modulated operating voltage 28 is applied to sensor heater 24. The pulse-width modulated operating voltage 28 is a digital signal, whose period duration and/or pulse control factor, that is, the ratio between the switch-on phase and the switch-off phase of the digital signal may be defined to be variable. By varying the period duration and in particular the pulse control factor, a mean operating voltage will be specified such that the heating power may be controlled or regulated in order to keep the operating temperature at a specified value or at least within a specified temperature range.

In principle, the temperature of sensor heater 24 could be measured directly and transmitted to pulse-width modulator 14 in exhaust-gas sensor electronic system 10 as an actual value. For the present purposes it is assumed that measuring signal 26 not only reflects a measure for the exhaust-gas variable to be detected, but also a measure for the operating temperature of measuring value detection device 22. For example, different time periods may be provided, the measuring variable to be detected being present in a first time period and a measure for the operating temperature being present in a second time period. If necessary, exhaust-gas sensor electronic system 10 may intervene in the measuring value detection device 22 of heatable exhaust-gas sensor 20 using a control signal (not shown) in order to ensure a separation between the exhaust-gas variable and the measure for the temperature.

It may be furthermore provided for exhaust-gas sensor 20 to transmit multiple measuring signals separately via different lines (not shown) to measuring signal evaluation device 12.

From the measure for the temperature of measuring value detection device 22, measuring signal evaluation device 12 ascertains the temperature signal 16, which reflects a measure for the actual temperature of measuring value detection device 22. Using the temperature signal 16, an intervention is made into pulse-width modulator 14 for defining the period duration and/or the pulse control factor and thus into the definition of the mean heating power in such a way that the actual temperature agrees with the specified setpoint temperature or lies within the specified setpoint temperature range.

The procedure according to the present invention provides for a priority of the measuring value detection with respect to the heating of heatable exhaust-gas sensor 20. Practice has shown that the pulse edges of pulse-width modulated operating voltage 28 may result in disturbances on the one hand in the at least one measuring signal 26 and on the other hand in measuring signal evaluation device 12.

Measuring signal evaluation device 12 knows when a measuring value is detected and/or when measuring signal 26 is evaluated. A corresponding time lapse of measuring signal detection processes is shown in FIG. 2a, the signal represented in FIG. 2a symbolizing the time windows 30, 32, in which the measuring value detection and/or the measuring signal evaluation occurs. At the same time, time windows 30, 32 reflect the occurrence of blocking signal 18. Blocking signal 18 thus occurs at the beginning 36 of time windows 30, 32 and ensures that pulse-width modulated operating voltage 28 is suppressed. Blocking signal 18 is withdrawn at the end 40, 42 of time windows 30, 32.

FIG. 2b, which shows pulse-width modulated operating voltage 28, shows the case in first time window 30 where a new pulse of pulse-width modulated operating voltage 28 would have occurred during the first time window 30 at a first time 44 if it had not been suppressed by blocking signal 18. A new pulse of pulse-width modulated operating voltage 28 may occur, however, only after the end 40 of first time window 30 on account of blocking signal 18.

If necessary, a delay time 46 is additionally provided such that the next pulse of pulse-width modulated operating voltage 28 may occur again at second time 48. Due to the time delay of the next pulse of pulse-width modulated operating voltage 28, an enlargement of the pulse control factor or the pulse duration at least of the next pulse may be provided so as to be able to maintain the mean heating power. The switch-off edge indicated by a dashed line would have occurred without the intervention by blocking signal 18.

Second time window 32 shows the case where the beginning 38 of second time window 32 would coincide with the switch-on edge of a pulse of pulse-width modulated operating voltage. On account of blocking signal 18 having occurred, however, the pulse is not supplied and is suppressed for the duration of second time window 32. The next pulse then occurs only after the end 42 of second time window 32, delayed, if necessary, by additional delay time 46. In this case too, it may be necessary to extend the subsequent pulse, which begins at fourth time 52, in order to ensure the maintenance of the mean heating power. In the case of this pulse as well, a switch-off edge is indicated by a dashed line, which would have occurred without the intervention of blocking signal 18.

Figure 3:
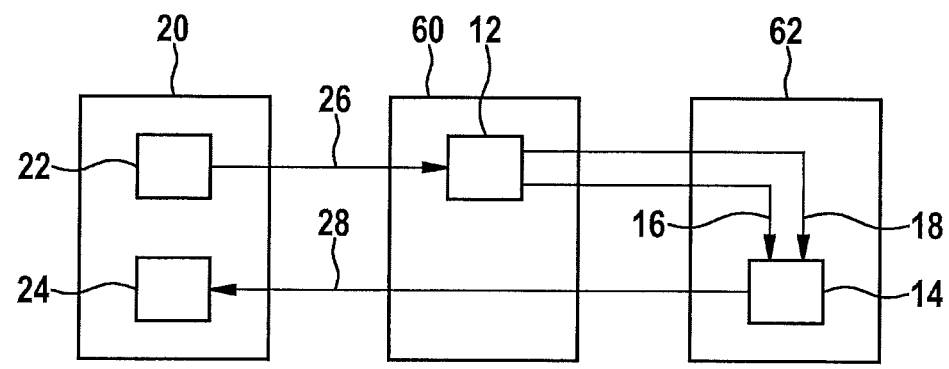
FIG. 3 shows a development of a device according to the present invention having a heatable exhaust-gas sensor and having both an exhaust-gas sensor electronic system as well as a switching device.

In the development of the device according to the present invention shown in FIG. 3, an exhaust-gas sensor electronic system 60 contains only measuring signal evaluation device 12. In addition to exhaust-gas sensor electronic system 60, a separate switching device 62 is provided, which contains at least pulse-width modulator 14. This development is preferably provided if exhaust-gas sensor electronic system 60 is accommodated in closer proximity to heatable exhaust-gas sensor 20, for example in a plug-connector housing. Here it must be noted that pulse-width modulator 14 is a power electronic system, which must be able to provide up to 20 watts of electrical power for sensor heater 24 such that an integration into the housing of a plug-connector, for example, is not always possible. Moreover, the advantage from the spatial separation, namely the electrical decoupling between the sensitive measuring signal evaluation device 12 and the power circuit of pulse-width modulator 14, would not be achieved.

Temperature signal 16 and blocking signal 18, which are provided by measuring signal evaluation device 12, are transmitted via at least one signal line to switching device 62. FIG. 3 shows a development having two separate lines.

Pulse-width modulated operating voltage 28 is transmitted from switching device 62 to sensor heater 24, the line being run through exhaust-gas sensor electronic system 60 if applicable, as indicated in FIG. 3.

The development shown in FIG. 3 works in the same manner as the development shown in FIG. 1 such that reference is made to the method of functioning described above.

The alternative development of the device according to the present invention shown in FIG. 4 is again based on an exhaust-gas sensor electronic system 70 and a separate switching device 72. In this arrangement it is assumed that exhaust-gas sensor electronic system 70 and switching device 72 work in a clock-synchronized manner, a joint clock signal 74 being provided both to exhaust-gas sensor electronic system 70 as well as to switching device 72. As a result, switching device 72 fundamentally knows precisely the time of a measuring value detection and/or a measuring signal evaluation within time windows 30, 32. Due to the clock synchronization, both the beginning 36, 38 as well as the end 40, 42 of the measuring windows 30, 32 are in each instance known both to measuring signal evaluation device 12 as well as to switching device 72.

Switching device 72 contains a sequence control system 76, in which the temporal positions of time windows 30, 32 or respectively the beginning 36, 38 and respectively the end 40, 42 of measuring windows 30, 32 are stored such that sequence control system 76 itself is able to supply blocking signal 18, which blocks pulse-width modulator 14 at least during measuring windows 30, 32.

Figure 4:
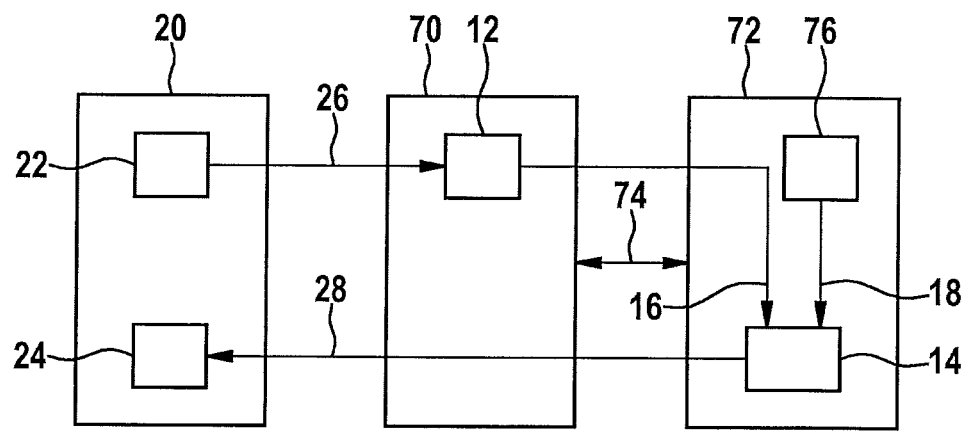
FIG. 4 shows an alternative development of a device according to the present invention having a heatable exhaust-gas sensor and having both an exhaust-gas sensor electronic system as well as a switching device.

The advantage of the arrangement shown in FIG. 4 as compared to the arrangements shown in FIGS. 1 and 3 lies in the fact that due to the knowledge of the temporal position of measuring windows 30, 32, the sequence control system 76 is able to supply blocking signal 18 already prior to the beginning 36, 38 of time windows 30, 32 respectively and thus is able to intervene in the supply of the pulse-width modulated operating voltage 28 already prior to the respective beginning 36, 38 of measuring windows 30, 32.

Figure 5A:
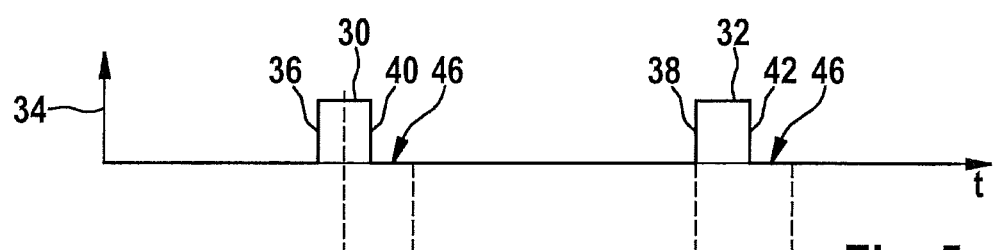
FIG. 5a shows again a time lapse of measuring signal detection processes.
Figure 5B:
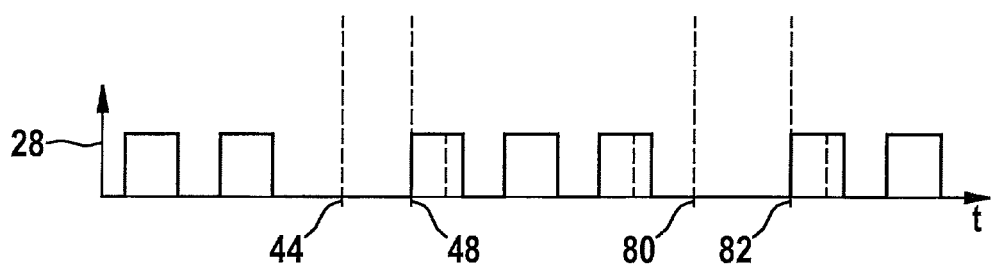
FIG. 5b shows again a pulse-width modulated operating voltage.

The corresponding time lapses are shown in FIGS. 5a and 5b. While in the range of the first time window 30 the time lapses agree with the time lapses shown in FIGS. 2a and 2b, in second time window 32 the case is to occur that blocking signal 18 is used to intervene in the last pulse of pulse-width modulated operating voltage 28 already prior to the beginning 38 of second time window 32. The switch-off edge of the pulse-width modulated operating voltage 28 of the last pulse prior to second time window 32, which is drawn as a dashed line represents the case without intervention of blocking signal 18. Because of the temporal position of second measuring window 32, which is known in sequence control system 76, the last pulse of pulse-width modulated operating voltage 28 may be extended prior to the occurrence of second time window 32 up to maximally the beginning 38 of second time window 32. The advantage of this measure lies in the fact that a drop of the mean heating power, which cannot be avoided entirely during timing windows 30, 32, may be counteracted already in advance by enlarging the pulse control factor, that is, by an extension of the pulse duration at least of the last pulse prior to a time window 30, 32.

Of course, due to the presence of blocking signal 18, a possible pulse of pulse-width modulated operating voltage 28 is suppressed at a fifth point in time 80 at least until the end 42 of second time window 32, delay time 46 being provided here again, if applicable, such that the first pulse after second time window 32 begins at a sixth point in time 82 with the switch-on edge. At least the first subsequent pulse following a time window 30, 32 may be extended again in order to counteract a drop of the mean heating power.

What is claimed is:

1. A method for operating a heatable exhaust-gas sensor, comprising:
   detecting, by the exhaust-gas sensor, at least one measuring signal; and
   operating a sensor heater using a pulse-width modulated operating voltage;
   wherein the detection of the at least one measuring signal has a higher priority over the supply of the pulse-width modulated operating voltage for the sensor heater, and at least during a predefined measuring time window in which the measuring signal is detected, the pulse-width modulated operating voltage that is supplied for the sensor heater is suppressed by supplying a blocking signal to an input of a pulse-width modulator that supplies the pulse-width modulated operating voltage to the sensor heater.

2. The method as recited in claim 1, wherein:
   the at least one measuring signal is detected by an evaluation device contained in an electronic system of the exhaust-gas sensor;
   the pulse-width modulator is contained in the electronic system of the exhaust-gas sensor; and
   the evaluation device supplies the blocking signal to the pulse-width modulator.

3. The method as recited in claim 1, wherein:
   the at least one measuring signal is detected by an evaluation device contained in an electronic system of the exhaust-gas sensor;
   the pulse-width modulator is contained in a switching device; and
   the evaluation device supplies the blocking signal to the pulse-width modulator contained in the switching device.

4. The method as recited in claim 1, wherein:
   the at least one measuring signal is detected by an evaluation device contained in an electronic system of the exhaust-gas sensor;
   the pulse-width modulator is contained in a switching device;
   the electronic system of the exhaust-gas sensor and the switching device work in a clock-synchronized manner;
   points in time defining the predefined measuring window are stored in a sequence control system of the switching device; and the sequence control system supplies the blocking signal to the pulse-width modulator.

5. The method as recited in claim 1, further comprising: providing a predefined delay time following the blocking signal, wherein following the predefined delay time, a pulse of the pulse-width modulated operating voltage is supplied again for the sensor heater.

6. The method as recited in claim 1, wherein a pulse of the pulse-width modulated operating voltage that is one of prior to and after the predefined measuring time window is extended in relation to other pulses of the pulse-width modulated operating voltage.

7. A control device for operating a heatable exhaust-gas sensor which supplies at least one measuring signal and in which a sensor heater is operated using a pulse-width modulated operating voltage, comprising:
   an exhaust-gas sensor electronic system which contains (i) a measuring signal evaluation device for evaluating the at least one measuring signal supplied by the heatable exhaust-gas sensor, and (ii) a pulse-width modulator for supplying the pulse-width modulated operating voltage for the sensor heater, wherein the measuring signal evaluation device supplies a blocking signal to an input of the pulse-width modulator, wherein the pulse-width modulated operating voltage is suppressed by the blocking signal.

8. The device as recited in claim 7, wherein the pulse-width modulator is contained in a switching device.

9. The control device as recited in claim 7, wherein a pulse of the pulse-width modulated operating voltage that is one of prior to and after a predefined measuring time window in which the measuring signal is detected is extended in relation to other pulses of the pulse-width modulated operating voltage.

10. A control device for operating a heatable exhaust-gas sensor which supplies at least one measuring signal and in which a sensor heater is operated using a pulse-width modulated operating voltage, comprising:
   an exhaust-gas sensor electronic system which contains (i) a measuring signal evaluation device for evaluating the at least one measuring signal supplied by the heatable exhaust-gas sensor, and (ii) a pulse-width modulator for supplying the pulse-width modulated operating voltage for the sensor heater, wherein the pulse-width modulator is contained in a switching device, and wherein the switching device furthermore contains a sequence control system which supplies a blocking signal for the pulse-width modulator to an input of the pulse-width modulator, wherein the pulse-width modulated operating voltage is suppressed by the blocking signal.

11. The control device as recited in claim 10, wherein a pulse of the pulse-width modulated operating voltage that is one of prior to and after a predefined measuring time window in which the measuring signal is detected is extended in relation to other pulses of the pulse-width modulated operating voltage.

* * * * *